United States Patent [19]

Brown et al.

[11] Patent Number: 4,738,259
[45] Date of Patent: Apr. 19, 1988

[54] DENTAL APPLIANCE FOR WEIGHT CONTROL

[76] Inventors: Steven J. Brown, 3633 S. 900 East #25, Salt Lake City, Utah 84106; Charles E. Comstock, 5871 Ayrshire Dr., Murray, Utah 84107

[21] Appl. No.: 878,970
[22] PCT Filed: Sep. 17, 1984
[86] PCT No.: PCT/US84/01483
 § 371 Date: May 16, 1986
 § 102(e) Date: May 16, 1986
[87] PCT Pub. No.: WO86/01706
 PCT Pub. Date: Mar. 27, 1986
[51] Int. Cl.⁴ ............................................. A61F 5/46
[52] U.S. Cl. .................... 128/136; 128/132 R; 128/155; 433/7
[58] Field of Search ............... 128/133, 136, 137; 433/6, 7

[56] References Cited

U.S. PATENT DOCUMENTS

| | | | |
|---|---|---|---|
| 2,593,821 | 4/1952 | Welch | 128/136 |
| 3,307,539 | 3/1967 | Petersen | 128/136 |
| 3,818,906 | 6/1974 | Stubbs | 128/136 |
| 4,211,008 | 7/1980 | Lerman | 433/6 X |
| 4,439,149 | 3/1984 | Devincenzo | 433/6 |
| 4,471,771 | 9/1984 | Brown et al. | 128/136 |

Primary Examiner—Mickey Yu
Attorney, Agent, or Firm—Thorpe, North & Western

[57] ABSTRACT

A weight control device (10) and method for disrupting natural mastication and transport of food at chewing surfaces of the teeth (12), to thereby impede the rate of food consumption and provide an appliance useful for weight reduction. The device comprises an doutwardly projecting wing-guard or flange (14, 15, 40), which is attached by a support collar (11) to the posterior teeth along a distal to mesial orientation. The flange (14, 15, 40) is positioned laterally of the teeth and above the chewing surfaces, with the upper portion inclined away from the teeth and the relative movement of the teeth during occlusion. The corresponding inventive methods comprise the steps of (i) interposing a blocking member (14, 15) between the food manipulating muscles such as the tongue, and the chewing surfaces of the teeth; and/or (ii) intermittently interposing a blocking member (40) between the chewing surfaces of the individual's teeth in response to food within the mouth to intermittently preclude occlusion of the teeth for mastication.

20 Claims, 1 Drawing Sheet

DENTAL APPLIANCE FOR WEIGHT CONTROL

BACKGROUND OF THE INVENTION

The importance of maintaining proper weight for good health continues to receive increased public attention. Such increased attention adds to the frustration of overweight persons who not only desire better health, but are also conscious of their overweight appearance. In serious cases, effective weight control is best accomplished by initially coordinating training in mental discipline with specific physiological measures. Such physiological measures may be necessary because overweight persons who have made repeated attempts to lose weight experience demoralizing frustration with each successive failure. The use of more stringent methods which supplement individual self discipline by physiologically forcing a change in eating habits may be helpful in re-establishing self confidence.

The parent U.S. Pat. No. 4,471,771 discloses a general method of weight control wherein mechanical devices are used to slow down the eating process to allow the body time to naturally register the sensation of having hunger satisfied prior to the completion of a meal. It is well known, for example, that the digestive system requires approximately 15 minutes of processing time before the brain registers satisfaction of the hunger sensation. Consequently, persons who eat quickly may consume much more food than is physiologically necessary for satisfaction of hunger. The referenced patent focuses on the method of impeding the eating process by providing a blocking device which at least partially obstructs the passage of unchewed, solid foods through the mouth to the stomach. By increasing the time duration food is retained in the mouth, one automatically reduces the rate of food consumption. Accordingly, the use of dental devices which are retained at tooth structure has proven to be an effective method for weight control, when used independently or in conjunction with diets or other weight loss methods. The present disclosure constitutes an improvement subsumed within the general method set forth and claimed in U.S. Pat. No. 4,471,771.

OBJECTS AND SUMMARY OF THE INVENTION

It is an object of this invention to provide a device or appliance for attachment to an individual's teeth for interfering with natural mastication and transport of food within the individual's mouth, thereby impeding the rate of food consumption.

It is a further object of the present invention to provide a dental appliance which impedes the passage of unchewed solid foods through the mouth to the stomach by limiting or restricting the free movement of food across the surfaces of the molars.

A further object of this invention is to impede the eating process by blocking access of the tongue to food as it is being chewed, thereby slowing down the natural process of mastication.

A still further object of the present invention is to increase the amount of effort required to chew food, thereby increasing the required time for consumption and decreasing the normal satisfaction of eating.

An additional object of the present invention is to provide a device which blocks unrestrained mastication by imposing a temporary obstacle between the occluding teeth.

These and other objects are realized in a weight loss device which comprises an outwardly projecting wing-guard or flange having an elongated configuration which is adapted to impede the passage of food there through. This flange or wing-guard projects above the chewing surfaces of the tooth and is mounted along a distal to mesial orientation at the side of the teeth such that the flange is positioned above the chewing surfaces and with the upper portion inclined away from the region between opposing teeth which occlude for mastication. Ideally, the flange or wing-guard is positioned between the tongue and teeth and prevents the tongue from manipulating the food in its customary manner. In addition, the flange prevents the food from moving freely to the tongue and into the stomach without complete mastication. With respect to more serious overweight conditions, the flange may be hinged at an upper portion to permit displacement of this upper portion to a collapsed configuration between the opposing surfaces of occluding teeth. The existence of the hinged portion of the flange requires the individual to physically raise the hinge from its interstitial position between the teeth before being able to chew any food. Typically, this will be accomplished by the tongue, which can lift the hinged member into its projecting, open configuration which allows occlusion. However, as the tongue and food move within the mouth, the hinged member again falls into its interstitial location, again requiring the individual to lift the hinge free of the chewing region.

These devices physiologically impede the eating process by creating mechanical obstacles to normal mastication, disrupting the emotional satisfaction of eating and by increasing the amount of effort required to consume a small portion of food. Both the physiological and psychological effects combine to enable weight loss where conventional methods have proven unsuccessful.

Other objects and features will be apparent to those skilled in the art, based upon the following detailed description, taken in combination with accompanying drawings.

DETAILED DESCRIPTION OF THE DRAWINGS

DETAILED DESCRIPTION OF BEST MODE

Figure 1:
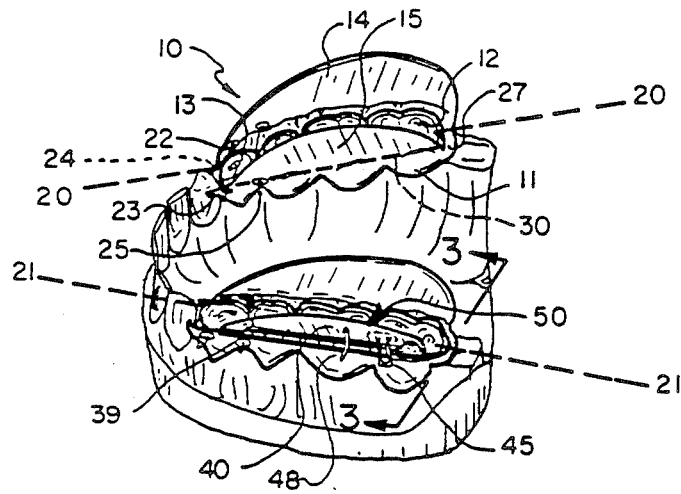
FIG. 1 shows a perspective view of a simulated oral environment having two attached embodiments of the subject weight control device.

Referring Now to the Drawings:

FIG. 1 shows a weight loss appliance 10 which comprises a support collar 11 adapted for attachment around the individual's tooth structure 12. Because of the primary purpose of interrupting or interfering with the chewing process, the device 10 is mounted around several of the molars. It will be apparent to those skilled in the art that the device can also extend forward to the pre-molar teeth 13 or bicuspids. In the configuration illustrated in FIG. 1, only the incisor and canine teeth remain unaffected. Accordingly, unrestrained chewing action is restricted to these forward teeth which are not adapted for mastication. It will be apparent from this disclosure that a primary benefit of the present invention is to interfere with natural mastication and transport of food within an individual's mouth. The implementation of this objective is detailed hereafter.

Figure 2:
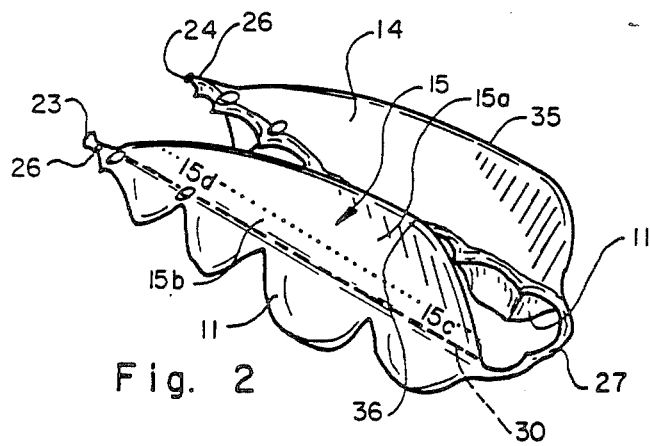
FIG. 2 is an isolated perspective view of a single appliance constructed in accordance with the present invention.
Figure 4:
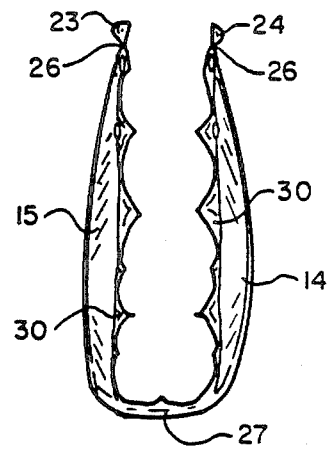
FIG. 4 is a top view of the device shown in FIG. 2.

The support collar 11 provides means for mounting a wing-guard or flange 14 or 15 to the teeth along a distal to mesial orientation 20 or 21. This collar or mounting means 11 may be constructed of banding material similar to that used in orthodontics or it may be structured pursuant to an impression of the attached teeth 12-13 and molded from chromium cobalt or other materials compatible with the oral environment. The preferred embodiment is illustrated as a molded structure which conforms to the configuration of the teeth to provide maximum support to the respective wing-guards or flanges (referred to hereafter as flanges) 14 and 15. The forward portion of the support collar is anchored in place by wires 22 tied to projecting fingers 23 and 24 (concealed on hidden side of denture). Additional wires 25 may be applied to insure adequate support for the attached appliance 10. The back portion of the collar or mounting means is retained in place by a bridging crossmember 27. As is shown in FIGS. 2 and 4, the preferred embodiment of the collar comprises a structure wherein the collar 11 is joined by the bridge 27 to form a three-sided enclosure which permits the appliance to be seated in place around the back molars from the distal side, with the forward end of the appliance being wired in place through the teeth at the respective fingers 23 and 24. A slot or groove 26 is provided to insure retention of the wires thereon. The procedures for constructing the support collar 11 with brace 27 are in conformance with standard procedures for taking impressions in wax, burning out the wax and casting the appliance in chrome cobalt. Soldered joints and wire are conventional materials used in orthodontics.

The function of the support collar is to provide a base for supporting one or both of the respective flanges 14 and 15. For purposes of description, reference is made to an upper mounting edge 30 which represents an imaginary line in the drawings to distinguish between the support collar 11 and the flange 15. It will be noted that the preferred embodiment is a single, integral structure which is fabricated as a single element by the previously discussed casting technique. Reference to the mounting edge 30 has been included in view of the numerous structures which are envisioned, including structures which may be of two or more parts. Although the mounting edge is somewhat figurative in the illustrative embodiments, it is useful for explaining the separate functions of the support collar 11 and the respective flange elements 14 and 15.

Accordingly, general reference is made to an upper mounting edge 30 which is aligned and positioned along the distal to mesial line 20 such that the flange mounted thereat 15 is oriented in a single distal to mesial line at the side of the teeth. This attachment edge 30 is illustrated as separated from and below the chewing surfaces of the teeth because the primary function of the support collar 11 does not involve obstruction of food or of the tongue.

Figure 3:
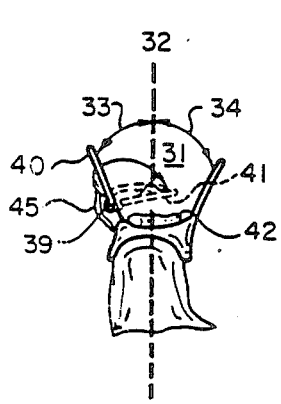
FIG. 3 is a plan view taken along the lines 3—3 of FIG. 1.

In addition to positioning and separating the wing-guard or flange laterally of the teeth and between opposing chewing surfaces, the support collar also positions the flange with the upper portion 15a projecting upward and inclined away from the chewing region 31 which exists between corresponding posterior teeth in the upper and lower jaws. This inclined orientation is generally described with respect to an imaginary vertical plane defined by the direction of relative movement of the opposing teeth which occlude adjacent the wing-guard or flange. This imaginary plane is identified in FIG. 3 as item 32. The exact angle of inclination 33 or 34 will depend upon the dentition, palate, cheek, tongue and free way space required. Likewise, the same factors determine the relative height of the respective flanges 14 and 15, as well as their contours. A typical flange height will range from one-half to one and a half centimeters.

Although the figures show each appliance 10 having a pair of flanges 14 and 15, a single flange may also be applied. Typically, this will be a lingual flange 15 which is attached at the mounting edge 30 and projects outward therefrom at a slightly inclined orientation with respect to the imaginary plane 32 defined by the direction of relative teeth movement during mastication of food at the respective teeth surfaces. Hereagain, the single lingual flange is positioned above the chewing surface of the teeth thereby forming an obstruction toward movement of food onto or away from the chewing surface. Typically, the lingual flange is an elongated, flat structure having a contoured upper edge 35 which is configured in shape and form to avoid contact with palatal tissue when the teeth are in an occluding position. Such contact may result in irritations which would unnecessarily add to the discomfort of the dieting patient.

It will be apparent to those skilled in the art that the configuration of this contoured edge will likely differ with each individual, based on the specific oral cavity structure. Generally, however, an appliance 10 attached at the posterior molars is likely to have a lingual flange which is greater in height at the distal side 15c than at the mesial side 15d. It is important to fabricate the flange 15 with sufficient height to insure adequate performance of its blocking function with respect to food and the tongue. It would be apparent to one skilled in the art that the actual dimensions and configuration of the wing-guard will be customed designed (i) to preserve proper spacial relationship between the tongue and palate such that the guard does not restrain the tongue from its normal speech function, and (ii) to prevent harmful contact leading to irritation at the palate or cheek. These respective design characteristics must be considered in connection with determining the appropriate height of the flange or wing-guard for performance of its blocking function. A proper evaluation and coordination of these various design parameters will be known to those skilled in the art. Obviously, these characteristics will also differ, depending on the number of teeth to which the appliance is applied. To insure proper support and functioning of the appliance, it is best to attach the device to at least three posterior teeth, including two molars, with the flange having sufficient length to bridge the distance of at least two of the attached teeth.

Just as the single flange can be attached at the lingual side, a buccal flange or wing-guard may be attached at the opposite side of the teeth, either in single or joint configuration with respect to the lingual flange. This buccal flange would be attached to a buccal mounting edge (figurative in the preferred embodiments disclosed herein) which is oriented along the distal to mesial line adjacent and below the buccal chewing surfaces of the teeth. The buccal flange is attached at the mounting edge and projects outward from the teeth at a slightly inclined orientation with respect to the plane of teeth movement 32. Hereagain, the buccal flange is positioned above the chewing surface of the teeth to form an obstruction toward movement of food onto or away from the chewing area. The flange is useful because of the movement of food by the cheek muscle which enhances mastication and speeds up the chewing process. By shielding this cheek muscle, mastication is impeded, further extending the time required for the eating process.

The general function of the lingual flange is to impede movement of food to and from the area of mastication. Where the overweight condition is not serious, a single flange may be adequate to correct the overweight condition. The single flange provides less restriction and discomfort within the mouth, yet operates to slow down the eating process to allow time for the digestive system to register any satisfaction of hunger. It also tends to increase the amount of mastication for food which is retained in place at the chewing surfaces of the teeth. This further enhances digestion and extends the eating process. A second flange, such as a buccal flange, further restricts food movement and enhances mastication by retaining food within a channel formed between the respective flanges. Where the length of the flange extends along the distance of several contiguous teeth, it would be difficult for the tongue to manipulate food into and out of the chewing area. A flange of shorter length permits the tongue to be more active in the positioning and displacement of food at the chewing surface. Therefore, it will be apparent that part of the process of customizing an appliance to a specific individual will be to evaluate the seriousness of the overweight problem, the ability of the user to restrain his/her diet and the configuration of the oral environment with respect to the shape, size and number of flanges or wing-guards necessary to disrupt the patient's eating habits.

In extreme cases where mere blocking of the tongue and food transport fails to realize desired weight loss results, an additional impediment can be added to the flanged structure. This second method involves the use of a hinged, upper section 40 of the flange 50. The hinge 39 is formed by severing the upper and lower portions of the flange and by soldering the orthodontic tube and inserted hinge wire at respective sides of the severed flange portion. This and comparable construction methods are well within the ability of those skilled in the art. This hinged configuration, shown as a buccal flange in FIGS. 1 and 3, functions not only to block access to the chewing area, but also to physically interfere with occlusion of the teeth when it is rotated to a collapsed configuration 41 (shown in phantom line in FIG. 3) wherein the flange section 40 is displaced from its outward projecting configuration to a collapsed configuration near the chewing surface 42 of the teeth to which it is attached. For a buccal, hinged flange, the collapsed position 41 can be initiated by the cheek muscle or by food rolling across its outer surface. In either case, the flange must be raised to its projected orientation 40 by the tongue or finger. The position of the hinge 39 at the top of the flange virtually requires each occlusion of the teeth to be followed by replacement of the flange to its projected orientation 40. It should be noted that the hinged location 39 may vary; however, a suitable hinge position is slightly above the mounting edge and at a uniform height with respect to the chewing surface. This will insure that contact between the collapsed flange and the teeth does not cause localized stress at a single point at the tooth structure. Obviously, safety considerations dictate spreading the occlusion forces over a broad surface area of the collapsed flange.

In addition, a stop 45 or other blocking member is soldered to the flange for preventing the hinged portion 40 of the flange from collapsing buccally beyond its inclined orientation and out of its blocking position. Failure to provide means for preventing rotation or collapse of the hinged portion away from the teeth would defeat the purpose of the flange, which could then fall free of the blocking position.

With respect to the closed or collapsed configuration 41 of the hinge, the structure must be adapted to preserve natural free way space in the interstitial region between the occluding teeth. Adequate free way space would permit the individual to speak, breath and sleep with adequate space between the collapsed hinge and opposing teeth from those teeth to which the appliance is attached. Typically, this free way space will span a distance of two to five milimeters.

Although the drawings illustrate a buccal flange with an upper hinge member 40, the preferred location for the hinged member would be on the lingual flange. The buccal flange is illustrated in the drawings because of its preferred position for viewing the hinge structure. As with the buccal flange, the lingual flange may be hinged between the upper portion 15a and lower portion 15b as is shown by the dotted line in FIG. 2. In addition to a simple hinge structure, a spring-biasing member 48 may be provided for biasing the guard to a closed, collapsed position. Under such circumstances, the chewing process is severely restricted and requires the individual to raise the flange sequentially between each chewing action. The degree of tension applied by the spring-biasing member 48 may be adjusted in accordance with the specific oral environment and needs of the individual. Where circumstances favor spring-biasing the hinge member to an open, projecting position as shown with item 40, the same structure may be utilized with appropriate positioning of the spring member 48. This open position may be desirable to allow free movement for food which has been thoroughly masticated. The biased hinge will deflect, however, where large particles of food are positioned at the lingual surface of the hinge, such as where too much food is taken into the mouth. Spring-biasing the hinge to an open position also reduces the discomfort of inadvertent collapse of the flange during movements of the mouth other than eating, such as in speech, etc.

The previously described structure has been applied as part of a weight loss/control program which has proven extremely effective, even with difficult weight loss cases. The method generally comprises the steps of (i) securing a food blocking device such as the flanged structured disclosed herein to the teeth inside the mouth in a position which impedes injested, unchewed, solid foods from being passed from the mouth to the stomach. Use of the subject device does not impede movement of the lower jaw, nor does it obstruct emergent foods from the stomach from being rejected by the body. The inventive method is further practiced by retaining this device within the mouth for sufficient time to result in a desired loss of weight.

More specifically, the inventive method disclosed herein is characterized by the steps of (i) interposing a blocking member, such as a buccal or lingual flange, between food manipulating muscles within the mouth and the chewing surfaces of the teeth such that free passage of food to the chewing surfaces is impeded; and (ii) maintaining the blocking member in this blocking position for sufficient number of continuous days to disrupt the normal eating habits of the individual. Such disruption results from the attendent difficulty of chewing and manipulating food wherein the food manipulating muscles such as the cheek and tongue are partially restrained.

Similarly, a second method of assisting an individual to lose weight by impeding the eating process, with the attendent advantages, is represented by the steps of (i) intermittently interposing a blocking member between the chewing surfaces of an individual's teeth, responsive to movement of food within the mouth, to thereby intermittently preclude occlusion of the teeth for mastication; and (ii) maintaining such intermittent interference over a sufficient number of days to interfere with the individual's eating habits and cause a resultant loss of weight. This intermittent blocking member corresponds to the hinged flange previously described as item 40 in the drawings. It will be apparent from the previous discussion that this blocking member is substantially retained free of contact with the chewing surfaces of the teeth during non-eating activity. Additional methods and variations of the disclosed weight loss methods will be apparent to those skilled in the art based on the foregoing disclosure.

Actual use of the weight loss devices and methods described herein have confirmed their utility. The average patient experiences a loss of approximately thirteen (13) pounds without the presence of an interstitial blocking hinge during the first month. Use of the hinge greatly increases weight loss because of the difficulty of eating where the hinge must be continually repositioned to the projecting position 40. In comparison with devices which bridge between posterior teeth as disclosed in the parent patent, the present invention maintains blocking structure in the area of the teeth, without interfering with the rest of the oral cavity. Discomfort is minimal and non-eating activities such as talking, sleeping, etc. are substantially unimpeded. Nevertheless, the presence of the flange structures are a constant reminder, both physiologically and psychologically, of the dieting process. Forgetfullness is extremely difficult because the mastication process of the tongue, cheek and teeth is restrained each time food enters the mouth. In otherwords, all eating must be accomplished "despite" the presence of food blocking structure at the teeth. Furthermore, because the user must brush the teeth and attached blocking structure after each meal, in between eating is severely restricted.

Obviously, good dental hygeine and extra care must be exercised when using this type of weight loss device. The oral environment must be clean. There can be no peridontal disease or other conditions which are incompatible with utilization of the teeth structure to support the required appliance. A unique advantage of the subject invention is that occlusion contact is preserved, despite the use of the teeth to support the referenced blocking structure. Absent such occlusion, teeth are likely to erupt and result in damage to the dentition and temporal mandibular joint. With appropriate dental and hygenic precautions, the subject weight loss method has proven to be a very practical and effective weight loss program.

We claim:

1. A device for attachment to an individual's teeth for interfering with natural mastication and transport of food within an individual's mouth to thereby impede the rate of food consumption and provide an appliance useful for weight reduction for overweight persons, said device comprising:

a support collar adapted for attachment around a portion of at least one tooth and having an upper mounting edge which is adapted to be aligned and positioned along the distal to mesial line at a lingual side and separated from chewing surfaces of the teeth to which it is to be attached; and a lingual flange attached at the mounting edge and adapted to project upward from attached lower teeth or downward from attached upper teeth and outward therefrom along the distal to mesial line and at an inclined orientation with respect to a plane defined by the direction of relative teeth movement during mastication of food at the tooth surface, said lingual flange being adapted to be at least partially positioned laterally of the chewing region between opposing surfaces of the teeth to thereby form an impeding surfaces of the teeth to thereby form an impeding obstruction against movement of food onto or away from the chewing surfaces.

2. A device as defined in claim 1, wherein the lingual flange is an elongated, flat structure having a contoured upper edge which is configured in shape and form to avoid contact with palatal tissue when the teeth are in an occluding position.

3. A device as defined in claim 2, wherein the collar is adapted to be attached to at least one molar and the lingual flange is greater in height at the distal side than at the correspnding mesial side of the tooth.

4. A device as defined in claim 2, wherein the collar is adapted to be attached to at least three posterior teeth, including two molars, said lingual flange having sufficient length to bridge the distance of at least two of the attached teeth.

5. A device as defined in claim 1, wherein the lingual flange is hinged at an upper portion thereof beyond the mounting edge to permit the hinged portion to displace from its outward projecting configuration to a collapsed configuration between the opposing teeth to chewing surfaces of the which it is adapted to be attached, and further comprising means for preventing the hinged portion of the flange from collapsing lingually beyond its inclined orientation and out of its lateral blocking position.

6. A device as defined in claim 1, wherein the support collar further includes an upper buccal mounting edge adapted to be positioned along the distal to mesial line adjacent and separated from buccal chewing surfaces of the teeth, said device further comprising a buccal flange attached at the buccal mounting edge and adapted to project outward from the chewing region of the teeth at a slightly inclined orientation with respect to a plane defined by the direction of relative teeth movement during mastication of food at the tooth surface of the teeth to thereby form an obstruction toward movement of food onto or away from the chewing surfaces.

7. A device as defined in claim 6, wherein the collar is adapted to be attached to at least three posterior teeth, including two molars, said lingual and buccal flanges having sufficient length to bridge the distance of at least two of the attached teeth.

8. A device as defined in claim 1, wherein the buccal flange is hinged at an upper portion thereof beyond the mounting edge to permit the hinged portion to displace from its outward projecting configuration to a collapsed configuration between the opposing chewing surfaces of the teeth to which it is adapted to be attached, and further comprising means for preventing the hinged portion of the flange from collapsing buccally beyond its inclined orientation and out of its lateral blocking position.

9. A device as defined in claim 5 wherein the hinged portion of lingual flange is adapted to collapse to an interstitial position between the opposing chewing surfaces of the the teeth which preserves the natural free way space therebetween.

10. A device as defined in claim 1, wherein the support collar and lingual flange are formed as a single integral structure which can be attached to the teeth as a single appliance, said collar being case or otherwise molded to conform to the shape of an impression taken of the teeth to which it is attached.

11. A weight control device for interfering with natural mastication and transport of food at a chewing region between opposing chewing surfaces of teeth within an individual's mouth to thereby impede the rate of food consumption and provide an appliance useful for weight reduction for overweight persons, said device comprising a wing-guard adapted to project laterally of the chewing region to impede the passage of food therethrough, said wing-guard having a flat, elongated configuration with an upper portion and unattached edge free of sharp corners and being adapted in size to project laterally of chewing surfaces of the teeth when properly positioned in the mouth, and means for mounting the wing-guard to the teeth along distal to mesial orientation and having a location with respect to the teeth such that the wing-guard is adapted to be positioned laterally of the teeth (ii) above and chewing surfaces and with the upper portion inclined away from a vertical plane defined by the direction of relative movement of opposing teeth which occlude adjacent the wing-guard, said device being thereby adapted to impede transfer of food and access of the individual's tongue to the chewing region between the opposing teeth.

12. A device as defined in claim 11 wherein the wing-guard is attached to the mounting means for positioning in a lingual orientation at posterior teeth.

13. A device as defined in claim 11 wherein the wing-guard is attached to the mounting means for positioning in a buccal orientation at posterior teeth.

14. A device as defined in claim 11 wherein the dimensions and configuration of the wing-guard are sufficiently inclined (i) to preserve spacial relationship between the tongue and palate such that the guard does not restrain the tongue from its normal speech function, and (ii) to prevent harmful contact leading to irriation by the wing-guard at the palate or cheek.

15. A device as defined in claim 11, wherein the upper portion of the flange is coupled to the lower portion of the guard by hinge means to permit the hinged portion to displace from its projecting configuration to a partially collapsed configuration between the opposing teeth to which it is to be attached, and further comprising means for preventing the hinged upper portion of the flange from collapsing away from the attached teeth beyond its inclined orientation and out of its lateral blocking position.

16. A device as defined in claim 11 wherein the device comprises both lingual and buccal wing-guards positioned on opposing sides of the mounting means, said guards forming a diverging channel between which the nonattached, occluding teeth come to rest when the teeth are in a closed position.

17. A device as defined in claim 11 wherein the configuration of the wing-guard and mounting means are formed from an impression mold taken from lower, posterior teeth and palate, thereby adapting the device for positioning at the lower teeth location.

18. A device as defined in claim 11 wherein the configuration of the wing-guard and mounting means are formed from an impression mold taken from upper, posterior teeth and palate, thereby adapting the device for positioning at the upper teeth location.

19. A device as defined in claim 15 wherein the upper, hinged portion of the guard includes means for spring biasing the guard to a closed, collapsed position, thereby requiring the individual to physically reposition the hinged portion to an open, projecting position or during the process of eating in order to bring the teeth into an occluding relationship.

20. A device as defined in claim 15 wherein the upper, hinged portion of the guard includes means for spring biasing the guard to an open, projecting position, thereby urging the hinged portion to the open, projecting position during speech and other non-eating activity, while permitting deflection of the hinge during the process of eating.

* * * * *